United States Patent
Shenai-Khatkhate et al.

(10) Patent No.: US 6,660,874 B2
(45) Date of Patent: Dec. 9, 2003

(54) TRIALKYL GROUP VA METAL COMPOUNDS

(75) Inventors: Deodatta V. Shenai-Khatkhate, Danvers, MA (US); Michael B. Power, Newburyport, MA (US); Artashes Amamchyan, Wakefield, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 10/118,382

(22) Filed: Apr. 6, 2002

(65) Prior Publication Data
US 2002/0188145 A1 Dec. 12, 2002

Related U.S. Application Data

(60) Provisional application No. 60/281,977, filed on Apr. 6, 2001.

(51) Int. Cl.$^7$ .................... C07F 9/00; C23C 16/00; C09K 19/00
(52) U.S. Cl. ............... 556/70; 427/248.1; 427/588; 428/1.1; 257/49
(58) Field of Search ................ 556/70; 427/588, 427/248.1; 428/1.1; 257/49

(56) References Cited

U.S. PATENT DOCUMENTS

| | | | | |
|---|---|---|---|---|
| 3,103,526 A | * | 9/1963 | Jenker | 556/70 |
| 3,137,716 A | * | 6/1964 | Stamm et al. | 556/70 |
| 4,906,762 A | | 3/1990 | Sawara et al. | 556/70 |
| 5,003,093 A | * | 3/1991 | Valentine, Jr. | 556/70 |
| 5,326,425 A | * | 7/1994 | Gedridge, Jr. | 117/104 |

OTHER PUBLICATIONS

Gimmnich et al., Material Science and Engineering, B17 (1993) 21–24.*
Schumann et al., Journal of Organometallic Chemistry, vol. 87, No. 1, pp. 83–92 (1975).*
Zakharkin et al., "Synthesis of Organometallic Compounds From Trialkylaluminums and Metal Salts", Bull. Acad. Sci. USSR, 1959, pp. 1853–1858.
Y. Takashi, "Organometallic Complexes Containing Antimony and Aluminum", J. Organometal. Chem., 8 (1967) pp. 225–231.
J. Eisch, "Organometallic Compounds of Group III. The Preparation of Gallium and Indium Alkyls from Organoaluminum Compounds", Journal of the American Chemical Society, vol. 84, No. 19, Oct. 1962, pp. 3605–3610.
Takashi et al., "Organometallic Complexes Containing Antimony and Aluminum I. Complex Formation of Alkylantimony Compounds with Aluminum Compounds", J. Organometal. Chem., 8 (1967) pp. 209–223.
Stringfellow, *Organometallic Vapor Phase Epitaxy: Theory and Practice*, Academic Press, 2$^{nd}$ Edition, 1999, pp. 1–16.

* cited by examiner

Primary Examiner—Porfirio Nazario-Gonzalez
(74) Attorney, Agent, or Firm—S. Matthew Cairns

(57) ABSTRACT

Disclosed are methods of preparing trialkyl Group VA metal compounds in high yield and high purity. Such trialkyl Group VA metal compounds are substantially free of oxygenated impurities, ethereal solvents and metallic impurities.

18 Claims, No Drawings

TRIALKYL GROUP VA METAL COMPOUNDS

This application claims the benefit of U.S. Provisional Application No. 60/281,977 filing date Apr. 6, 2001.

BACKGROUND OF THE INVENTION

The present invention relates generally to the field of organometallic compounds. In particular, the present invention relates to trialkyl Group VA metal compounds which are suitable for use as precursors for chemical vapor deposition.

Metal films may be deposited on surfaces, such as non-conductive surfaces, by a variety of means such as chemical vapor deposition ("CVD"), physical vapor deposition ("PVD"), and other epitaxial techniques such as liquid phase epitaxy ("LPE"), molecular beam epitaxy ("MBE"), and chemical beam epitaxy ("CBE"). Chemical vapor deposition processes, such as metalorganic chemical vapor deposition ("MOCVD"), deposit a metal layer by decomposing organometallic precursor compounds at elevated temperatures, i.e. above room temperature, either at atmospheric pressure or at reduced pressures.

A wide variety of metals may be deposited using such CVD or MOCVD processes. See, for example, Stringfellow, *Organometallic Vapor Phase Epitaxy: Theory and Practice*, Academic Press, 2$^{nd}$ Edition, 1999, for an overview of such processes. Organometallic compounds of arsenic, antimony, and bismuth are used to deposit epitaxial films in the semiconductor and related electronic industries. Epitaxial films such as gallium arsenide find applications in optoelectronic devices such as detectors, solar cells, light-emitting diodes ("LED's"), lasers and electronic switching devices such as field effect transistors ("FET's") and high electron mobility FET's ("HEMT's"). Ternary arsenic alloys also exist such as gallium indium arsenide ("GaInAs") and aluminum indium arsenide ("AlInAs"), which are more attractive than GaAs or aluminum gallium arsenide ("AlGaAs") for the most powerful fiber optic systems operating in the 1.3 to 1.55 micron wavelength range. Gallium arsenide phosphide ("GaAsP") is suitable for visible LED's and fiber optic emitters/detectors. Trimethylarsine in particular has been used as a precursor for carbon doping. Antimony and antimony alloy films are useful in fiber optics communication systems, particularly in the 1.3 and 1.55-micron regions. Antimony-containing semiconductor materials also have commercial applications including detection for seeker, night vision and surveillance devices (infrared detectors) and sources (LED's or lasers). A variety of binary, ternary and quaternary Group III/V semiconductor systems containing antimony have been evaluated for applications in infrared emitters and detectors operating in the 3 to 5 micron and 8 to 12 micron spectral ranges. These wavelength ranges are important since they are natural windows in the atmosphere for infrared transmission. Epitaxial antimony-based Group III/V semiconductors have potential applications in long wavelength detectors and high-speed electronic devices.

For such semiconductor and electronic device applications, these Group VA metal alkyls must be highly pure and be substantially free of detectable levels of both metallic impurities, such as silicon and zinc, as well as oxygenated impurities. Oxygenated impurities are typically present from the solvents used to prepare such organometallic compounds, and are also present from other adventitious sources of moisture or oxygen.

The most common method of preparing Group VA metal alkyl compounds consists of reacting Group VA metal trihalides with Grignard reagents in an ethereal solvent, such as alkyl ethers, glymes or tetrahydrofuran. Aluminum alkyls can also be used instead of Grignard reagents in the preparation of Group VA metal alkyl compounds. For example, Zakharkin et al., *Bull. Acad. Sci. USSR*, 1959, p1853, discloses a method of producing trialkyl compounds of antimony and bismuth, as shown in equation (I), where R is ethyl, n-propyl or iso-butyl and X is chloride or fluoride.

$$MX_3 + R_3Al + \text{diethylether} \rightarrow MR_3 + AlX_3 \qquad (I)$$

Trace amounts of ethereal solvent invariably remain in the target organometallic compound obtained using conventional techniques. Such residual ethereal solvent contributes oxygen as a deleterious impurity in metal films deposited from such precursor compounds.

Attempts have been made to synthesize Group VA organometallics in non-ethereal solvents. For example, Takashi et al., *J. Organometal. Chem.*, 8, pp 209–223, 1967, disclose the reaction of antimony trichloride with triethylaluminum in hexane. Such reaction was found to produce triethylstibine in extremely low yields (only about 10%), the remainder being about 42% metallic antimony and about 46% of an antimony-aluminum complex, $(SbEt_4)(Al_2Et_5Cl_2)$. This article does not teach how to obtain triethylstibines free of antimony-aluminum complexes.

U.S. Pat. No. 4,906,762 (Sawara et al.) discloses a method of producing pure trialkylarsines from aluminum alkyls and diarsenic trioxide using alkali metal halides as complexing agents in hydrocarbon solvents. The method constitutes a two-step synthesis, both stages being heterogeneous reactions with final yields not more than 65%, and rendering highly reactive/pyrophoric reaction residues. Tertiary amines are not disclosed in this patent.

There is thus a need for methods for preparing Group VA metal alkyls in high yields with less reactive reaction residues and for Group VA metal compounds substantially free of both metallic and oxygenated impurities for use as precursor compounds for CVD.

SUMMARY OF THE INVENTION

It has been found that Group VA metal alkyls can be prepared in high yield and in high purity by reacting Group VA trihalides and Group IIIA alkyls in the presence of tertiary amines in hydrocarbon solvents. Group VA alkyl compounds produced by this method are extremely pure and substantially free of oxygenated impurities.

In one aspect, the present invention provides a method for preparing trialkyl Group VA metal compounds including the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3.

In a second aspect, the present invention provides a method for depositing a film of a Group VA metal on a substrate including the steps of: a) conveying a Group VA metal source compound in the gaseous phase to a deposition chamber containing the substrate; b) decomposing the Group VA metal source compound in the deposition chamber; and c) depositing a film of the Group VA metal on the substrate; wherein the Group VA metal source compound is prepared by the method including the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$ alkyl; $M^1$ is a Group IIIA metal; X is halogen and n is an integer from 1–3.

In a third aspect, the present invention provides a method for manufacturing an electronic device including the step of depositing a film of a Group VA metal on an electronic device substrate including the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound is prepared by the method including the step of reacting a Group VA metal trihalide with a trialkyl Group IIIA compound of the formula $R_nM^1X_{3-n}$ in the presence of a tertiary amine in an organic solvent that is free of oxygen substitution, wherein each R is independently selected from $(C_1-C_6)$ alkyl; $M^1$ is a Group IIIA metal; X is halogen and n is an integer from 1–3.

In another aspect, the present invention provides trialkylantimony compounds substantially free of ethereal solvents. In still another aspect, the present invention provides trialkylbismuth compounds substantially free of ethereal solvents.

DETAILED DESCRIPTION OF THE INVENTION

As used throughout this specification, the following abbreviations shall have the following meanings, unless the context clearly indicates otherwise: ° C.=degrees centigrade; NMR=nuclear magnetic resonance; mtorr=millitorr; g=gram; L=liter; ca.=approximately; mm=millimeters; and mL=milliliter.

"Halogen" refers to fluorine, chlorine, bromine and iodide and "halo" refers to fluoro, chloro, bromo and iodo. Likewise, "halogenated" refers to fluorinated, chlorinated, brominated and iodinated. "Alkyl" includes linear, branched and cyclic alkyl. Unless otherwise noted, all amounts are percent by weight and all ratios are molar ratios. All numerical ranges are inclusive and combinable in any order.

The present invention provides a method for preparing trialkyl Group VA metal compounds including the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3. Preferred Group VA metals include antimony ("Sb"), arsenic ("As") and bismuth ("Bi"). Suitable Group VA trihalides are those having the general formula $MX_3$, where M is a Group VA metal and each X is independently fluorine, chlorine, bromine or iodine. It is preferred that X is chlorine, bromine or iodine. Group VA trichlorides are more preferred. Particularly suitable Group VA metal halides include, but are not limited to, antimony trichloride, antimony tribromide, antimony triiodide, arsenic trichloride, arsenic tribromide, arsenic triiodide, bismuth trichloride, bismuth tribromide, bismuth triiodide and mixtures thereof. It will be appreciated that mixed halide compounds may also be advantageously used in the present invention. Such Group VA metal trihalides are generally commercially available from a variety of sources or may be prepared by a variety of methods known in the literature.

A wide variety of Group IIIA compounds may be used in the present invention. Suitable Group IIIA compounds useful in the present invention typically have the formula $R_nM^1X_{3-n}$, wherein each R is independently selected from $(C_1-C_6)$alkyl; $M^1$ is a Group IIIA metal; X is halogen; and n is an integer from 1 to 3. $M^1$ is suitably boron, aluminum, gallium, indium and thallium. Preferably, X is selected from fluorine, chlorine or bromine. Suitable alkyl groups for R include, but are not limited to, methyl, ethyl, n-propyl, iso-propyl, n-butyl, iso-butyl, tert-butyl, and the like. Preferred alkyls include, methyl, ethyl, n-propyl and iso-propyl. In one embodiment, it is preferred that n is 3. Such Group IIIA compounds where n is 3 include trialkylboron, trialkylaluminum, dialkylaluminum halide, trialkylgallium, trialkylindium and trialkylthallium, with trialkylaluminum compounds being preferred. In an alternate embodiment, it is preferred that n is 1 or 2. Such Group IIIA compounds where n is 1–2 include dialkylaluminum chlorides. Group IIIA compounds are generally commercially from a variety of sources or may be prepared by a variety of methods known in the literature.

Any tertiary amine may suitably be used in the present invention. Suitable tertiary amines include, but are not limited to, those having the general formula $NR^4R^5R^6$, wherein $R^4$, $R^5$ and $R^6$ are independently selected from $(C_1-C_6)$alkyl, $di(C_1-C_6)$alkylamino-substituted $(C_1-C_6)$ alkyl, and phenyl and wherein $R^4$ and $R^5$ may be taken together along with the nitrogen to which they are attached to form a 5–7 membered heterocyclic ring. Such heterocyclic ring may be aromatic or non-aromatic. Particularly suitable tertiary amines include, but are not limited to, trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N',N'-tetramethyl-1,2-diaminoethane, pyridine, pyrazine, pyrimidine, and mixtures thereof. Preferred amines include trimethylamine, triethylamine, tri-n-propylamine, triiso-propylamine, and tri-n-butylamine. More preferably, the tertiary amine is triethylamine or tri-n-propylamine. It will be appreciated by those skilled in the art that more than one tertiary amine may be used in the present invention. Such tertiary amines are generally commercially available from a variety of sources. Such tertiary amines may be used as is or, preferably further purified prior to use.

A wide variety of organic solvents may be used in the present invention, provided that such organic solvents do not contain oxygenated species. It is further preferred that the organic solvents do not contain oxygen. Particularly suitable organic solvents include, but are not limited to, hydrocarbons and aromatic hydrocarbons. Preferred organic solvents include benzene, toluene, xylene, pentane, hexane, heptane, octane, decane, dodecane, squalane, cyclopentane, cyclohexane, cycloheptane, and mixtures thereof. More preferably, the organic solvent is benzene, toluene, xylene, hexane, heptane, cyclopentane or cyclohexane. It will be appreciated that more than one organic solvent may be advantageously used in the present invention. In an alternative embodiment, the tertiary amine may be used as the organic solvent. Such organic solvents are generally commercially available from a variety of sources. Such solvents may be used as is or, preferably, purified prior to use.

Preferably, such organic solvents are deoxygenated prior to use. The solvents may be deoxygenated by a variety of means, such as purging with an inert gas, degassing the solvent in vacuo, or a combination thereof. Suitable inert gases include argon, nitrogen and helium, and preferably argon or nitrogen.

In the process of the present invention, Group IIIA compound, tertiary amine and organic solvent may be combined in any order prior to reacting with the Group VA metal trihalide. Preferably, the Group IIIA compound is first combined with the tertiary amine to form an amine-Group IIIA adduct. Typically, the amine-Group IIIA adduct may be formed at a wide variety of temperatures. Suitable temperatures for forming the adduct are from ambient to 90° C. The Group VA metal trihalide is then reacted with the amine-Group IIIA adduct to form the desired trialkyl Group VA metal compound. It is preferred that the Group VA metal trihalide is added dropwise, either neat or as a hydrocarbon solution, to the amine-Group IIIA adduct. Suitable temperatures to form the trialkyl Group VA compound are from about ambient to 80° C. A wide variety of tertiary amines and organic solvents may be used in the present invention. Thus, in a preferred embodiment, the present invention provides a method for preparing trialkyl Group VA metal compounds including the steps of reacting a Group IIIA compound with a tertiary amine to form an amine-Group IIIA adduct in an organic solvent that is free of oxygenated species; and reacting the amine-Group IIIA adduct with a Group VA metal trihalide in the organic solvent. It is further preferred that the Group IIIA compound is a trialkylaluminum or dialkylaluminum chloride.

In general, the tertiary amine is present in a stoichiometric amount to the Group IIIA compound. The amount of Group VA trihalide is, typically, in a stoichiometric amount to the Group IIIA compound, the stoichiometry being dependent on the nature of Group IIIA compound, Group VA compound, and the tertiary amine selected. The molar ratio of Group IIIA to Group VA Compound ranges from 1 to 3. It is anticipated that molar ratios greater than 3 will also be effective.

The specific tertiary amine and organic solvent used depend upon the particular trialkyl Group VA compound desired. For example, the organic solvent and tertiary amine may be selected such that they are more volatile or less volatile than the desired trialkyl Group VA compound. Such differences in volatility provide easier separation of the trialkyl Group VA compound from both the amine and organic solvent. The trialkyl Group VA compounds of the present invention may be suitably purified by distillation.

An advantage of the present invention is that trialkyl Group VA compounds prepared are substantially free of ethereal solvents, and preferably free of ethereal solvents. A further advantage is that the trialkyl Group VA compounds are substantially free of metallic impurities, preferably they are substantially free of zinc and silicon. The present trialkyl Group VA compounds are substantially free of silicon. By "substantially free" it is meant that the present compounds contain less than 0.5 ppm of such impurities. For example, trimethylantimony prepared according to the present invention contains about 0.1 ppm silicon as compared to 2 ppm in conventionally prepared trimethylantimony. Trimethylarsenic prepared according to the present invention contains about 0.3 ppm silicon as compared to 3 ppm in conventionally prepared trimethylarsenic. A still further advantage is that the amount of air-sensitive reaction waste is reduced significantly as compared to conventional methods of preparation that typically generate either pyrophoric or highly toxic reaction residues. Trialkylantimony compounds prepared using conventional ethereal processes produce weak trialkyl antimony-ether complexes. Such complexes are very difficult to remove and can cause contamination in films produced from them. Such ether complexes are avoided by the present invention.

The present invention provides a trialkyl Group VA metal compound substantially free of ethereal solvents and aluminum complexes, wherein the Group VA metal compound is selected from trialkylstibine, trialkylarsine and trialkylbismuth. The present invention is particularly useful for preparing trimethyl Group VA compounds. Thus, the present invention further provides trimethyl Group VA metal compounds substantially free of ethereal solvents and aluminum complexes. Such trimethyl Group VA compounds are also substantially free of zinc and silicon. Preferred trimethyl Group VA compounds are trimethylstibine, trimethylarsine and trimethylbismuth. Thus, the present invention further provides trialkyl Group VA metal compounds that are substantially free of zinc and silicon, and preferably substantially free of zinc, silicon, ethereal solvents and aluminum complexes. Further, the present invention provides trialkylantimony compounds substantially free of ethereal solvents. Also provided by the present invention are trialkylbismuth compounds substantially free of ethereal solvents.

The trialkyl Group VA compounds are particularly suitable for use as precursors in CVD, and particularly MOCVD and metalorganic vapor phase epitaxy ("MOVPE"). The present trialkylstibine compounds are useful for depositing antimony films, the trialkylarsine compounds are useful for depositing arsenic films and the trialkylbismuth compounds are useful for depositing bismuth films. Such films are useful in the manufacture of electronic devices, such as integrated circuits, and optoelectronic devices. For example, trialkylstibine compounds are particularly useful in the production of antimony alloys suitable for use in fiber optic applications, particularly in the 1.3 and 1.55-micron regions. Antimony and antimony alloys are also useful in the 3 to 5 micron region for chemical sensors for infrared countermeasures, communications based on non-silicon dioxide fibers and thermophotovoltaic ("TPV") devices, and in the 8 to 12 micron region for night-vision devices and infrared imaging, and cryogenically cooled, high-mobility electronic devices for high speed.

Films of Group VA metals are typically deposited by first placing the desired trialkyl Group VA metal compound, i.e. source compound or precursor compound, in a bubbler having an outlet connected to a deposition chamber. A wide variety of bubblers may be used, depending upon the particular deposition apparatus used. The source compound is maintained in the bubbler as a liquid or solid. Solid source compounds are typically vaporized or sublimed prior to transportation to the deposition chamber. The source compound is typically transported to the deposition chamber by passing a carrier gas through the bubbler. Suitable carrier gasses include nitrogen, hydrogen, and mixtures thereof. In general, the carrier gas is introduced below the surface of the source compound, and bubbles up through the source compound to the headspace above it, entraining or carrying vapor of the source compound in the carrier gas. The entrained or carried vapor then passes into the deposition chamber.

The deposition chamber is typically a heated vessel within which is disposed at least one, and possibly many, substrates. The deposition chamber has an outlet, which is typically connected to a vacuum pump in order to draw by-products out of the chamber and to provide a reduced pressure where that is appropriate. MOCVD can be conducted at atmospheric or reduced pressure. The deposition chamber is maintained at a temperature sufficiently high to induce decomposition of the source compound. The typical deposition chamber temperature is from about 300° to about 1000° C., the exact temperature selected being optimized to provide efficient deposition. Optionally, the temperature in the deposition chamber as a whole can be reduced if the substrate is maintained at an elevated temperature, or if other energy such as radio frequency ("RF") energy is generated by an RF source.

Suitable substrates for deposition, in the case of electronic device manufacture, may be silicon, gallium arsenide, indium phosphide, and the like. Such substrates are particularly useful in the manufacture of integrated circuits.

Deposition is continued for as long as desired to produce a film having the desired properties. Typically, the film thickness will be from several hundred to several thousand angstroms or more when deposition is stopped.

Thus, the present invention provides a method for depositing a film of a Group VA metal on a substrate including the steps of: a) conveying a Group VA metal source compound in the gaseous phase to a deposition chamber containing the substrate; b) decomposing the Group VA metal source compound in the deposition chamber; and c) depositing a film of the Group VA metal on the substrate; wherein the Group VA metal compound is prepared by the method including the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3. In an alternate embodiment, the present invention provides a method for depositing a film of a Group VA metal on a substrate including the steps of depositing a film of a Group VA metal on a substrate including the steps of: a) conveying a trimethyl Group VA metal compound in the gaseous phase to a deposition chamber containing the substrate; b) decomposing the trimethyl Group VA metal compound in the deposition chamber; and c) depositing a film of the Group VA metal on the substrate; wherein the trimethyl Group VA metal compound is substantially free of ethereal solvents and aluminum complexes. In still another embodiment, the present invention provides a method for depositing a film of a Group VA metal on a substrate including the steps of depositing a film of a Group VA metal on a substrate including the steps of: a) conveying a trialkyl Group VA metal compound in the gaseous phase to a deposition chamber containing the substrate; b) decomposing the trialkyl Group VA metal compound in the deposition chamber; and c) depositing a film of the Group VA metal on the substrate; wherein the trialkyl Group VA metal compound is substantially free of ethereal solvents and aluminum complexes, wherein the Group VA metal compound is selected from trialkylstibine, trialkylarsine and trialkylbismuth.

The present invention further provides a method for manufacturing an electronic device including the step of depositing a film of a Group VA metal on an electronic device substrate including the steps of: a) conveying a Group VA metal source compound in the gaseous phase to a deposition chamber containing the substrate; b) decomposing the Group VA metal source compound in the deposition chamber; and c) depositing a film of the Group VA metal on the substrate; wherein the Group VA metal source compound is prepared by the method including the step of reacting a Group VA metal trihalide with a Group IIIA compound of the formula $R_nM_1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3. In another embodiment, the present invention provides a method for manufacturing an electronic device including the step of depositing a film of a Group VA metal on an electronic device substrate including the steps of: a) conveying a trimethyl Group VA metal compound in the gaseous phase to a deposition chamber containing the substrate; b) decomposing the trimethyl Group VA metal compound in the deposition chamber; and c) depositing a film of the Group VA metal on the substrate; wherein the trimethyl Group VA metal compound is substantially free of ethereal solvents and aluminum complexes. In a further embodiment, the present invention provides a method for manufacturing an electronic device including the step of depositing a film of a Group VA metal on an electronic device substrate including the steps of: a) conveying a trialkyl Group VA metal compound in the gaseous phase to a deposition chamber containing the substrate; b) decomposing the trialkyl Group VA metal compound in the deposition chamber; and c) depositing a film of the Group VA metal on the substrate; wherein the trialkyl Group VA metal compound is substantially free of ethereal solvents and aluminum complexes, wherein the Group VA metal compound is selected from trialkylstibine, trialkylarsine and trialkylbismuth.

The following examples are presented to illustrate further various aspects of the present invention, but are not intended to limit the scope of the invention in any aspect.

EXAMPLE 1

Antimony trichloride (114 g, 0.5 moles) was dissolved in ca. 150 mL of degassed xylene. This was added dropwise via pressure equalized dropping funnel under nitrogen to a stirred solution of an n-propylamine (95 mL, 0.5 moles)) adduct of trimethylaluminum (36 g, 0.5 moles) previously prepared in xylene (200 mL). During the addition, heat was evolved and toward the end of the addition, a small amount of black antimony metal was deposited. The complete addition took 2.5 hours. A stirrable black slurry resulted.

The desired trimethylstibine was distilled from the black slurry via a 2-foot vacuum jacketed column packed with stainless steel packing. Product began to reflux in the distillation head at 140° C. oil bath temperature. The head temperature remained steady at 80° C. The reflux ratio for collection was 1:1. Material collected over a 1-hour period from a pot temperature range between 140–160° C. The yield was 62 g (74%). $^1$H NMR of the trimethylstibine in $d_6$-benzene showed a singlet at 0.636 ppm.

EXAMPLE 2

In a glove bag, antimony trichloride (159 g, 0.7 moles) was charged into a 500 mL three-necked glass round bottomed flask. To this was added 200 g of degassed toluene, which completely dissolved the solid antimony trichloride upon gentle shaking.

Also in the glove bag were added triethylaluminum (80 g, 0.7 moles) and degassed toluene (300 g) to a 2 L three-necked round-bottomed flask equipped with a magnetic stir bar. To this solution was slowly added dropwise triethylamine (70.8 g, 0.7 moles) to form a toluene solution of the adduct. The adduct formation was accompanied by a small exotherm.

The flasks were taken out of the glove bag. The triethylaluminum-triethylamine ($Et_3Al$-$Et_3N$) adduct in toluene flask was equipped with a condenser on one side-neck (connected to nitrogen) and a pressure equalized dropping funnel on the other. Then the antimony trichloride/toluene solution was added via siphon to the dropping funnel. The antimony trichloride/toluene solution was then slowly added dropwise to the magnetically stirred $Et_3Al$-$Et_3N$ adduct in toluene at room temperature. Immediately a black precipitate began to form. The complete addition took 4 hours. Some heat was produced with the surrounding oil bath warming to 45° C. maximum during the addition.

After the reaction, the dropping funnel and condenser were removed from the flask. A pre-evacuated and nitrogen backfilled receiver flask was connected via flexible stainless steel U-tube. The receiver was cooled with dry-ice/isopropanol and the volatile contents of the reaction vessel were condensed under full vacuum (oil pump ca. 100 mtorr) in the receiver flask. The reaction vessel was warmed slowly during a 4-hour period under full vacuum to an oil bath temperature of 50° C. After cooling the system was then backfilled with nitrogen and a sample of the condensate was analyzed by NMR. The NMR indicated that there was approximately 135 g of triethylstibine ($Et_3Sb$) present out of a possible 146 g.

The final product was separated from toluene by partial pressure distillation using a stainless steel packed vacuum jacketed distillation column connected to a dry ice distillation head attached to two receiving flasks. The toluene was removed at 35 mm of mercury ("Hg") between pot temperatures of 43° to 53° C. (head temperature of 33–34° C.). Then the pressure was reduced to 12.5 mm of Hg and the final product collected in the second receiver. It distilled over at a pot temperature between 73–75° C. and a head temperature of 50–52° C. When the collection was complete, the system was backfilled with nitrogen. The yield was 100 g (68%). $^1H$ NMR of the triethylantimony in $d_6$-benzene showed a multiplet at 1.186 ppm.

EXAMPLE 3

Arsenic trichloride (85 g, 0.47 moles) was dissolved in 40 mL of degassed toluene and added dropwise via pressure equalized dropping funnel under nitrogen to a stirred solution of an n-triethylamine (49 g, 0.48 moles) adduct of trimethylaluminum (34.6 g, 0.48 moles) previously prepared in degassed toluene (70 mL). During the addition, heat was evolved and toward the end of the addition, a stirrable brown slurry resulted. The complete addition took 3 hours. The slurry was stirred for additional 1 hour at 80° C., then the crude product was distilled via Vigreux column yielding 63 g of material, containing trimethylarsine, toluene and traces of triethylamine, according to NMR data. Final distillation of crude material via packed vacuum-jacketed column gave 31 g (55%) of pure trimethylarsine. $^1H$ NMR of the trimethylarsenic in $d_6$-benzene showed a singlet at 0.778 ppm.

EXAMPLE 4

Arsenic trichloride (70 g, 0.38 moles) was dissolved in 40 mL of degassed toluene and added dropwise via pressure equalized dropping funnel under nitrogen to a stirred solution of an n-triethylamine (59 g, 0.58 moles) adduct of trimethylaluminum (41.8 g, 0.58 moles) previously prepared in degassed toluene (85 mL). During the addition, heat was evolved and toward the end of the addition, a stirrable brown slurry resulted. The complete addition took 3 hours. The slurry was stirred for additional 1 hour at 80° C., then the crude product was distilled via Vigreux column yielding 77 g of material, containing trimethylarsine, toluene and traces of triethylamine, according to NMR data. Final distillation of crude material via packed vacuum-jacketed column gave 38.1 g (82%) of pure trimethylarsine.

EXAMPLE 5

Arsenic trichloride (62 g, 0.34 moles) was dissolved in 35 mL of degassed toluene and added dropwise via pressure equalized dropping funnel under nitrogen to a stirred solution of an n-triethylamine (55 g, 0.54 moles) adduct of dimethylaluminum chloride (49 g, 0.53 moles) previously prepared in degassed toluene (70 mL). During the addition, heat was evolved and toward the end of the addition, a stirrable brown slurry resulted. The complete addition took 2 hours. The slurry was stirred for additional 1 hour at 80° C., then the crude product was distilled via Vigreux column yielding 40 g of material, containing trimethylarsine, toluene and traces of triethylamine, according to NMR data. Final distillation of crude material via packed vacuum-jacketed column gave 19 g (46%) of pure trimethylarsine.

What is claimed is:

1. A method for preparing trialkyl Group VA metal compounds comprising the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3.

2. The method of claim 1 wherein the organic solvent comprises aliphatic hydrocarbons or aromatic hydrocarbons.

3. The method of claim 2 wherein the organic solvent is selected from benzene, toluene, xylene, pentane, hexane, heptane, octane, decane, dodecane, squalane, cyclopentane, cyclohexane, cycloheptane, or mixtures thereof.

4. The method of claim 1 wherein n is 3.

5. The method of claim 1 wherein $M^1$ is selected from boron, aluminum, gallium, indium or thallium.

6. The method of claim 1 wherein n is 1–2.

7. The method of claim 1 wherein the Group VA metal trihalide is selected from antimony trihalide, arsenic trihalide or bismuth trihalide.

8. The method of claim 1 wherein the Group VA metal trihalide is selected from the group consisting of antimony trichloride, antimony tribromide, antimony triiodide, arsenic trichloride, arsenic tribromide, arsenic triodide, bismuth trichloride, bismuth tribromide, bismuth triiodide and mixtures thereof.

9. The method of claim 1 wherein the tertiary amine has the formula $NR^4R^5R^6$, wherein $R^4$, $R^5$ and $R^6$ are independently selected from $(C_1-C_6)$alkyl, $di(C_1-C_6)$alkylamino-substituted $(C_1-C_6)$alkyl and phenyl, and wherein $R^4$ and $R^5$ may be taken together along with the nitrogen to which they are attached to form a 5–7 membered heterocyclic ring.

10. The method of claim 1 wherein the tertiary amine is selected from trimethylamine, triethylamine, tri-n-propylamine, tri-n-butylamine, tri-iso-propylamine, tri-iso-butylamine, dimethylaminocyclohexane, diethylaminocyclohexane, dimethylaminocyclopentane, diethylaminocyclopentane, N-methylpyrrolidine, N-ethylpyrrolidine, N-n-propylpyrrolidine, N-iso-propylpyrrolidine, N-methylpiperidine, N-ethylpiperidine, N-n-propylpiperidine, N-iso-propylpiperidine, N,N'-dimethylpiperazine, N,N'-diethylpiperazine, N,N'-dipropylpiperazine, N,N,N',N'-tetramethyl-1,2-diaminoethane, pyridine, pyrazine, pyrimidine or mixtures thereof.

11. The method of claim 9 wherein the tertiary amine is selected from the group consisting of trimethylamine, triethylamine, tri-n-propylamine, triiso-propylamine, and tri-n-butylamine.

12. The method of claim 1 wherein the trialkyl Group VA metal compounds are substantially free of ethereal solvents and aluminum complexes.

13. A method for depositing a film of a Group VA metal on a substrate comprising the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound contains <0.5 ppm of ethereal solvents; and wherein the Group VA metal compound is a trialkylantimony compound or a trialkylbismuth compound.

14. A method for depositing a film of a Group VA metal on a substrate comprising the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound contains <0.5 ppm of ethereal solvents; and wherein the Group VA metal compound is prepared by the method comprising the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$alkyl; $M^1$ is a Group IIIA metal; X is halogen and n is an integer from 1–3.

15. The method of claim 14 wherein the Group VA metal compound contains <0.5 ppm of silicon.

16. A method for manufacturing an electronic device comprising the step of depositing a film of a Group VA metal on an electronic device substrate comprising the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound contains <0.5 ppm of ethereal solvents; and wherein the Group VA metal compound is a trialkylantimony compound or a trialkylbismuth compound.

17. A method for manufacturing an electronic device comprising the step of depositing a film of a Group VA metal on an electronic device substrate comprising the steps of: a) conveying a Group VA metal compound in the gaseous phase to a deposition chamber containing the substrate; b) decomposing the Group VA metal compound in the deposition chamber; and c) depositing a film of the Group VA metal on the substrate; wherein the Group VA metal compound contains <0.5 ppm of ethereal solvents; and wherein the Group VA metal compound is prepared by the method comprising the step of reacting a Group VA metal trihalide with a Group IIIA compound of the formula $R_nM^1X_{3-n}$ in the presence of a tertiary amine in an organic solvent that is free of oxygen substitution, wherein each R is independently selected from $(C_1-C_6)$ alkyl; $M^1$ is a Group IIIA metal; X is halogen and n is an integer from 1–3.

18. The method of claim 17 wherein the Group VA metal compound contains <0.5 ppm of silicon.

* * * * *